US006376679B2

(12) United States Patent
Leduc et al.

(10) Patent No.: US 6,376,679 B2
(45) Date of Patent: Apr. 23, 2002

(54) PHOTOPROTECTIVE/COSMETIC COMPOSITIONS COMPRISING NOVEL BENZ-$_X$-AZOLE-SUBSTITUTED SILANE/SILOXANE SUNSCREENS

(75) Inventors: Madeleine Leduc, Paris; Hervé Richard, Villepinte; Alain Lagrange, Coupvray, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/740,063

(22) Filed: Dec. 20, 2000

Related U.S. Application Data

(63) Continuation of application No. 09/205,607, filed on Dec. 4, 1998, now abandoned.

(30) Foreign Application Priority Data

Dec. 4, 1997 (FR) ............................................. 9715309

(51) Int. Cl.[7] .................... C07D 231/56; C07D 235/18; C07D 263/56; C07D 277/62; A61K 7/42; A61K 7/06; A61K 7/11

(52) U.S. Cl. .................. 548/110; 424/70.9; 424/70.12; 424/59; 424/40; 424/450

(58) Field of Search .......................... 548/110; 424/401, 424/450, 59, 70.9, 70.12

(56) References Cited

U.S. PATENT DOCUMENTS

| | | | | | |
|---|---|---|---|---|---|
| 4,316,033 | A | * | 2/1982 | Ching | 548/110 |
| 4,328,346 | A | * | 5/1982 | Chung et al. | 548/110 |
| 4,859,759 | A | * | 8/1989 | Maycock et al. | 524/27 |
| 4,960,898 | A | * | 10/1990 | Sakuta, I et al. | 548/110 |
| 5,102,707 | A | * | 4/1992 | Canivence et al. | 424/44 |
| 5,164,462 | A | * | 11/1992 | Yang | 525/478 |
| 5,254,542 | A | * | 10/1993 | Sakuta, III et al. | 514/63 |
| 5,569,451 | A | * | 10/1996 | Richard, I et al. | 424/59 |
| 5,610,257 | A | * | 3/1997 | Richard, II et al. | 528/15 |
| 5,663,270 | A | * | 9/1997 | Richard, III et al. | 528/27 |

FOREIGN PATENT DOCUMENTS

| | | | | |
|---|---|---|---|---|
| EP | 0282294 | * | 9/1986 | 548/110 |
| EP | 0712855 | | 5/1996 | |
| FR | 1241329 | | 12/1960 | |

* cited by examiner

*Primary Examiner*—Floyd D. Higel
(74) *Attorney, Agent, or Firm*—Burns, Doane, Swecker & Mathis, L.L.P.

(57) ABSTRACT

Photoprotective, topically applicable sunscreen/cosmetic compositions well suited for the UV-photoprotection of human skin and/or hair, comprise an effective UV-photoprotecting amount of at least one novel benz-x-azole-substituted silane or siloxane having the formula (1) or (2):

(1)

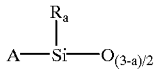

$$A—SiR'_1R'_2R'_3 \quad (2)$$

in which A is a radical having the structural formula (I):

(I)

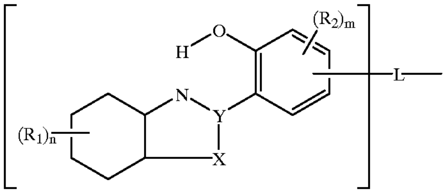

41 Claims, No Drawings

PHOTOPROTECTIVE/COSMETIC COMPOSITIONS COMPRISING NOVEL BENZ-$_X$-AZOLE-SUBSTITUTED SILANE/SILOXANE SUNSCREENS

This is a continuation application of U.S. patent application Ser. No. 09/205,607, filed on Dec. 4, 1998, now abandoned.

BACKGROUND OF THE INVENTION

1. Technical Field of the Invention

The invention concerns new silicon-bearing derivatives of benz-x-azole that are liposoluble, photostable, and have an excellent absorption power in the UV radiation spectrum. The invention also pertains to compositions, particularly cosmetic compositions, containing these new derivatives, which can be used for photoprotection of the skin and/or hair against UV radiation, particularly solar radiation.

2. Description of the Prior Art

It is a known fact that light radiation in the wavelength range of between 280 nm and 400 nm can darken the human epidermis and that, more specifically, radiation in the wavelength range of between 280 and 320 nm, referred to as UV-B, causes cutaneous erythema and burns which can be detrimental to the development of natural tanning. For these reasons, as well as for esthetic reasons, there is a growing demand for ways of controlling this natural tanning in order to control the color of one's skin. As a result, this UV-B radiation needs to be filtered out.

It is also a known fact that UV-A radiation, having a wavelength of between 320 and 400 nm, which causes the skin to tan, is likely to induce an alteration of the skin, particularly in the case of sensitive skin or skin that is continually exposed to solar radiation. In particular, UV-A rays cause the skin to lose its elasticity and wrinkles to appear, leading to premature skin aging. They promote the triggering of the erythematic reaction or amplify this reaction in certain subjects, and can even be the cause of phototoxic or photoallergic reactions. Consequently, for esthetic and cosmetic reasons, such as maintaining the natural elasticity of the skin, for example, more and more people wish to control the effect of UV-A radiation on their skin. It is therefore desirable to filter out UV-A radiation as well.

Numerous compounds intended for the photoprotection (UV-A and/or UV-B) of the skin have thus far been offered.

Most of them are aromatic compounds providing absorption of UV rays in the spectrum of between 280 and 315 nm, or in the spectrum of between 315 and 400 nm, or still in the combined spectrum of these two ranges. They are most often formulated in sunscreen compositions in the form of an oil-in-water emulsion (that is, a cosmetically acceptable medium consisting of a continuous aqueous dispersing phase and a discontinuous oily dispersed phase) and which therefore contain in various concentrations one or more conventional organic filters having an aromatic function which are lipophilic and/or hydrophilic and capable of selectively absorbing harmful UV radiation, with these filters (and their quantities) being selected according to the desired solar protection factor (the solar protection factor is expressed mathematically as the ratio of the necessary irradiation time to reach the erythematogenic threshold with the UV filter, to the time necessary to reach the erythematogenic threshold without the UV filter).

In addition to their filtration power, these anti-UV compounds must also have good cosmetic properties in the compositions containing them, good solubility in the usual solvents, especially fatty substances such as oils and greases, as well as good resistance to water and perspiration (persistence).

SUMMARY OF THE INVENTION

Among the aromatic compounds that have been proposed for this purpose we can mention the (hydroxy-2'-phenyl)-2-benz-x-azole compounds of patent application CH 350,763. The solubility of these molecules in various types of formulations used in the field of solar protection is still inadequate.

The Applicant made the surprising discovery of new silicon-bearing derivatives of benz-x-azole having improved properties, particularly with regard to their solubility in fatty substances and their stability with light.

More specifically, according to this invention it was found that by grafting one or more benz-x-azole groups to a silicone chain, it was possible to arrive at new compounds that, in addition to excellent filtering properties in the UV-A and/or UV-B radiation range, provide very good solubility in the commonly-used organic solvents and particularly fatty substances such as oils, as well as excellent cosmetic properties, making them particularly appropriate for use as solar radiation filters in, or for the preparation of, cosmetic compositions intended for the protection of the skin and/or hair against ultraviolet radiation.

DETAILED DESCRIPTION OF BEST MODE AND SPECIFIC/PREFERRED EMBODIMENTS OF THE INVENTION

Consequently, the first object of this invention is new compounds characterized by the fact that they have at least one unit based on the following formula (1) or (2):

(1)

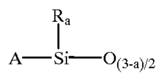

$$A—SiR'_1R'_2R'_3 \qquad (2)$$

in which:

- R refers to a hydrocarbonic group saturated or unsaturated at $C_1$–$C_{30}$, a hydrocarbonic group halogenated at $C_1$–$C_8$, or a trimethylsilyloxy group;
- a is equal to 1 or 2;
- $R'_1$, $R'_2$, and $R'_3$, either identical or different, are chosen from among the linear or branched, saturated or unsaturated alkyl and alkenyl radicals at $C_1$–$C_8$;
- A is a radical having the following formula (I):

(I)

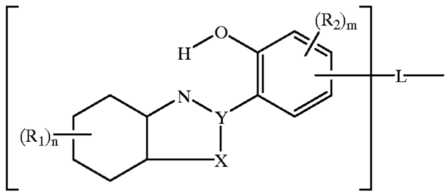

in which:

- L is a divalent radical allowing radical A to latch on to the silicone chain;

radicals $R_1$ and $R_2$, either identical or different, independently represent an atom of hydrogen, a linear or branched alkyl radical at $C_{1-C10}$, or a linear or branched alkenyl radical at $C_2$–$C_8$, with two adjacent $R_1$ or $R_2$ components being capable of forming an alkylidene dioxy group in which the alkylidene group contains 1 or 2 atoms of carbon;

Y represents C or N;

X represents O; $NR_3$; S when Y designates C or C when Y designates N;

$R_3$ is a hydrogen atom or an alkyl radical at $C_1$–$C_8$;

n and m are 1 or 2 independently.

Preferably, L satisfies one of the following formulas (a) or (a'):

(a)

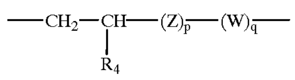

(a')

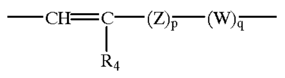

in which:

W represents O or NH;

Z is a linear or branched, saturated or unsaturated di-yl alkane radical at $C_1$–$C_6$, possibly substituted with a linear or branched, saturated or unsaturated hydroxyl or alkyl radical at $C_2$–$C_8$;

$R_4$ represents an atom of hydrogen, a hydroxyl radical, or a linear or branched, saturated or unsaturated alkyl radical at $C_{1-8}$;

p and q are 0 or 1.

Preferably, the compounds according to the invention satisfy one of the following two formulas (3 or 4):

(3)

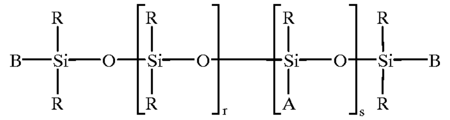

(4)

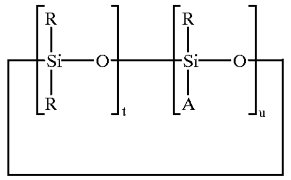

in which:

R designates a saturated or unsaturated hydrocarbonic group at $C_1$–$C_{30}$, a halogenated hydrocarbonic group at $C_1$–$C_8$, or a trimethylsilyloxy group;

the B components, either identical or different, are chosen from among the R radicals and the A radical;

r is a whole number of between 0 and 50 inclusively;

s is a whole number of between 0 and 20 inclusively and if s is 0, then at least one of the B symbols is A;

u is a whole number between 1 and 6 inclusively;

t is a whole number between 0 and 10 inclusively;

t+u is equal to or greater than 3.

The compounds of the invention display excellent liposolubility and can thus be used in large concentrations, thus providing the final compositions with very high protection indices; furthermore, they spread uniformly throughout conventional cosmetic media containing at least one fatty phase or a cosmetically acceptable organic solvent, and can thus be applied to the skin or the hair in order to act as an effective protective film.

In addition, the compounds of the invention have an excellent intrinsic filtration power with regard to UV-A and/or UV-B ultraviolet radiation.

These new silicon-bearing derivatives of benz-x-azole can therefore be used as sunscreens for human skin and hair. They can also be used as protective agents against light in the plastics industry.

Preferably, the R radicals, either identical or different, are chosen from among the linear or branched, saturated or unsaturated alkyl radicals at $C_1$–$C_{10}$, the phenyl radical, and the trifluoro-3,3,3-propyl radical, with at least 80% of the R radicals by number being the methyl radical.

In formulas (1) through (4) above, special preference is given to the statistical or block-defined derivatives having at least one of the following properties:

R is methyl

B is methyl $R_1$ is H $R_2$ is methyl or methoxy p is 1 q is 0 or 1

W is O r is between 0 and 3 inclusively s is between 1 and 3 inclusively t+u is between 3 and 5

$R'_1$, $R'_2$, and $R'_3$ are methyl.

In order to prepare the derivatives of formulas (1) through (4), one can proceed conventionally by implementing a hydrosilylation reaction starting with the corresponding siloxane or silane derivative in which, for example, all the A radicals are hydrogen atoms. This derivative is referred to as the SiH derivative in the remainder of the text.

The SiH groups can be present in the chain and/or at the end of the chain. These SiH derivatives are well known products in the silicone industry and are generally available on the market. They are described, for instance, in American patents U.S. Pat. Nos. 3,220,972, 3,697,473, and 4340709.

The SiH derivatives corresponding to the compounds of formulas (2), (3), and (4) can therefore be represented by the following formulas (5) through (7):

$$H\text{—}SiR'_1R'_2R'_3 \quad (5)$$

(6)

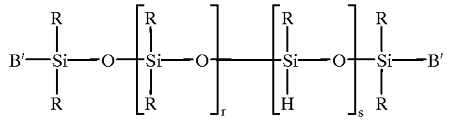

-continued (7)

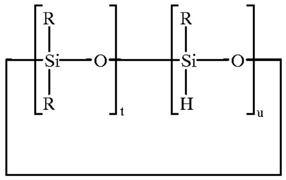

in which:

$R'_1$1, $R'_2$, and $R'_3$ have the meanings given above for formula (2);

R, r, s, t, and u have the meanings given above for formulas (3) and (4);

the B' components, either identical or different, are chosen from among the R radicals and a hydrogen atom.

In order to prepare the compounds of the invention per formulas (2) through (4) above, one proceeds in the following way: the SiH derivative per formula (5), (6), or (7) is caused to undergo a hydrosilylation reaction in the presence of a catalytically effective quantity of a platinum catalyst on an organic derivative of benz-x-azole chosen from among those of the following formula (I'):

(I')

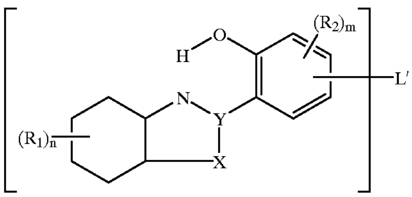

where $R_1$, $R_2$, X, Y, n, and m have the same meanings as for formula (I) above and L' complies with one of the following two formulas (b and b'):

$CH \equiv C-(Z)_{pl}-(W)_q-$tm (b')

(b)

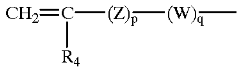

$CH \equiv C-(Z)_p-(W)_q-$ (b')

where W, R4, Z, p, and q have the same meanings as in formulas (a) and (a') above.

The hydrosilylation reaction is therefore conducted according to one of the following two reactions:

(grafting to formula (b))

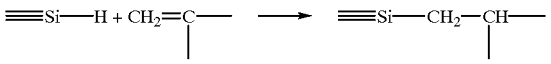

or

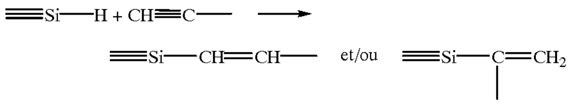

(grafting to formula (b'))

As benz-x-azole derivatives usable for the preparation of the compounds according to the invention, special preference goes to:

2-benzoxazol-2-yl-4-methyl-6-(2-methyl-allyl)-phenol 2-(1H-benzimidazol-2-yl)-4-methoxy-6-(2-methyl-allyl)-phenol The derivatives of formula (I') are obtained by condensation of an alkene or alkenyl halogenide with a derivative of formula (I")

(I")

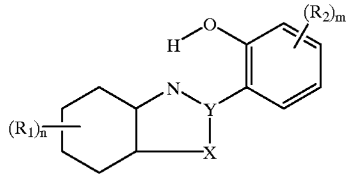

in which the $R_1$, $R_2$, X, Y, n, and m radicals have the same meanings as in formulas (I) and (I'); followed by a Claisen rearrangement reaction.

As benz-x-azole derivatives usable for the preparation of the compounds according to the invention per formula (I"), special preference goes to:

2-benzoxazol-2-yl-4-methyl-phenol 2-(1H-benzimidazol-2-yl)-4-methoxy-phenol

The formula (I") derivatives can be prepared according to the procedures described in patent CH 350,763.

The silane derivatives per formula (2) (A—Si—$R',R'_2R'_3$) according to the invention can be obtained using another synthesis process which involves starting with the derivative of the following formula (c):

(c)

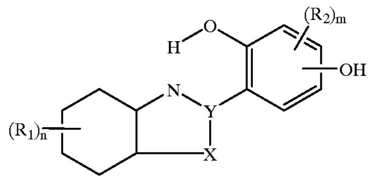

in which radicals $R_1$, $R_2$, X, Y, n, and m have the same meanings as for formulas (I) and (I') above, and by causing a silane derivative having the following formula (8) to react with it:

$$Hal-(Z)_p-CHR_4-CH_2-SiR'_1R'_2R'_3 \quad (8)$$

in which Hal represents a halogen and more specifically chlorine, and the radicals $R_4$, Z, $R'_1$, $R'_2$, $R'_3$, and p have the same meanings as above.

The derivatives of formula (c) can be prepared according to the procedures described in patent CH 350,763.

The silane derivatives per formula (2) (A—Si—$R'_1R'_2R'_3$) according to the invention can be obtained according to another synthesis process which involves starting with the derivatives of the following formula (9):

(9)

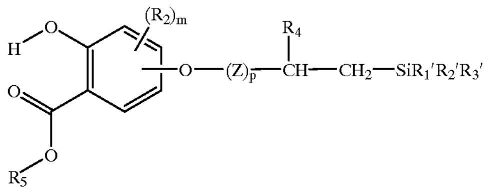

in which radicals $R_2$, $R_4$, Z, $R'_1$, $R'_2$, $R'_3$, and p have the same meanings as in the above formulas and $R_5$ is H or methyl, and by causing it to react with a derivative of the following formula (10):

(10)

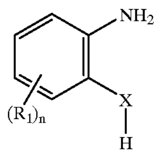

in which X has the same meaning as in the above formulas, with this cyclization condensation being possible in the presence of boric acid.

The derivatives of formula (9) are obtained by condensation of an alkene or alkenyl halogenide with a derivative of the following formula (11):

(11)

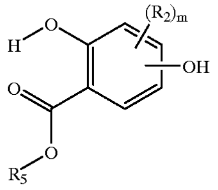

in which radicals $R_2$, $R_5$, and m have the same meanings as in formulas (I) and (9). The products of formulas (10) and (11) are commercial products.

The object of this invention is also a composition comprising a compound per formula (1) through (4) of the invention in an appropriate medium. The medium can be, for instance, a plastic material composition. It may also be appropriate for topical application. In this case the composition of the invention is a cosmetic composition which comprises a cosmetically acceptable medium.

The composition according to the invention is preferably a composition intended to protect a material sensitive to ultraviolet radiation, particularly solar radiation, comprising an effective quantity of at least one compound per the invention. In a preferred embodiment of the invention, this composition is intended to protect the skin and/or hair.

The compounds of formula (1), (2), (3), or (4) are generally present in the composition of the invention in proportions ranging between 0.1% and 20% by weight, preferably between 0.5% and 10% by weight, in relation to the total weight of the composition.

Naturally, the compositions according to the invention may contain one or more additional solar filters active in the UVA and/or UVB spectrum (absorbers) other than the compounds of this invention, be they hydrophilic or lipophilic. In particular, these additional filters may be chosen from among the cinnamic derivatives, the salicylic derivatives, derivatives of camphor, triazine derivatives, benzophenone derivatives, dibenzoylmethane derivatives, derivatives of beta,beta-diphenylacrylate, derivatives of p-aminobenzoic acid, and the filtering polymers and filtering silicones described in application WO-93/04665. Other examples of organic filters are given in patent application EP-A-0487404.

The compositions according to the invention may also contain skin tanning and/or artificial darkening agents (dyeing agents) such as dihydroxyacetone (DHA).

The compositions according to the invention may furthermore contain pigments or nanopigments (average size of primary particles: generally between 5 nm and 100 nm, preferably between 10 nm and 50 nm) of metal oxides, either coated or not, such as nanopigments of oxides of titanium (amorphous or crystallized in rutile and/or octahedrite form), iron, zinc, zirconium, or cerium which are all well-known UV photoprotective agents in their own right. Furthermore, conventional coating agents consist of alumina and/or aluminum stearate. Such nanopigments of metal oxides, either coated or not, are described in patent applications EP-A-0518772 and EP-A-0518773.

The composition may contain the cosmetic additives commonly used in the field of cosmetics, such as fatty substances, organic solvents, silicones, thickeners, softeners, additional sun filters, anti-foaming agents, hydrating agents, scents, preservatives, surface-active agents, fillers, complexing agents, anionic, cationic, non-ionic, or amphoteric polymers or their mixtures, propellants, alkalinizing or acidifying agents, dyes, pigments or nanopigments, particularly those intended to provide an additional photoprotective effect through physical blocking of the ultraviolet radiation, or any other ingredient generally used in cosmetics, especially for the manufacture of sunscreen compositions.

With regard to the organic solvents, we can mention the inferior alcohols and polyols such as ethanol, isopropanol, propyleneglycol, glycerin, and sorbitol.

The fatty substances may consist of an oil or a wax or their mixtures, fatty acids, esters of fatty acids, fatty alcohols, vaseline, paraffin, lanolin, hydrogenated lanolin, and acetylated lanolin. The oils can be selected from among animal, vegetable, mineral, or synthetic oils, particularly hydrogenated palm oil, hydrogenated ricin oil, vaseline oil, paraffin oil, Purcellin oil, silicone oils, either volatile or not, and isoparaffins.

Naturally, specialists in the field will be careful to choose the additional compound or compounds mentioned above and/or their quantities in such a way that the beneficial intrinsic properties of the compound according to the invention are not altered, at least not substantially, by the additive or additives in question.

The cosmetic composition of the invention can be used as a human epidermis or hair protection composition against ultraviolet rays, as a sunscreen composition, or as a make-up product.

The composition may occur in the form of a lotion, a thickened lotion, a gel, a creme, a milk, a powder, a solid stick, and may possibly be packaged as an aerosol in the form of a foam or spray.

When the cosmetic composition of the invention is specifically intended to protect the human epidermis against UV rays or as a sunscreen composition, it may occur in the form of a suspension or dispersion in solvents or fatty substances, or in the form of an emulsion (particularly an O/W or W/O emulsion, but preferably O/W) such as a creme or a milk, a vesicular dispersion, in the form of an ointment, gel, solid stick, or aerosol foam. The emulsions may furthermore contain anionic, non-ionic, cationic, or amphoteric surface-active agents.

When the cosmetic composition according to the invention is used to protect the hair, it can occur in the form of a shampoo, lotion, gel, or rinse composition to be applied before or after shampooing, before or after dyeing, before, during, or after a permanent or straightening treatment, a styling or treatment lotion or gel, a brushing or setting lotion or gel, hair spray, a permanent or straightening composition or a hair dyeing or bleaching composition.

When the cosmetic composition according to the invention is specifically intended for depigmentation of the skin, it may occur in all the galenical forms normally used for topical application, particularly in the form of an aqueous, hydroalcohol, or oily solution, an oil-in-water or water-in-oil emulsion or multiple emulsion, an aqueous or oily gel, a liquid, pasty, or solid anhydrous product, a dispersion of oil in an aqueous phase using spherules, with the spherules possibly being polymeric nanoparticles such as nanospheres and nanocapsules or, better still, ionic and/or non-ionic lipid vesicles.

The composition may be more or less fluid and have the appearance of a white or colored creme, an ointment, a milk, a lotion, a serum, a paste, or a foam. It could possibly be applied to the skin in an aerosol form. It can also occur in a solid form and, for instance, in the form of a stick.

When the cosmetic composition according to the invention is used as an eyelash, eyebrow, skin or hair make-up product, such as a skin treatment creme, foundation, lipstick, eye shadow, rouge, eye liner, mascara, or coloring gel, it can occur in a solid or pasty, anhydrous or aqueous form, such as oil-in-water or water-in-oil emulsions, suspensions, or gels.

The object of the invention is furthermore the use of a compound complying with the invention in or for the manufacture of compositions intended to protect materials sensitive to ultraviolet radiation, particularly solar radiation.

The object of the invention is furthermore a compound per formula (1), (2), (3), or (4) complying with the invention for the preparation of a medication intended to prevent the harmful effects of UV radiation.

Finally, the object of the invention is a cosmetic process for protecting the skin and/or hair against ultraviolet radiation, particularly solar radiation, which involves the application of an effective quantity of the cosmetic composition defined above, or a compound per formula (1), (2), (3), or (4) as defined earlier, to the skin or hair.

The examples which follow illustrate the invention without, however, limiting its scope.

EXAMPLE OF PREPARATION 1

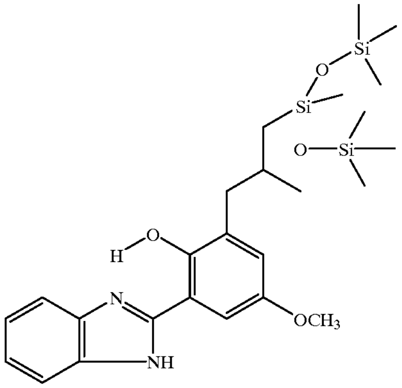

a) First stage: preparation of 2-[5-methoxy-2-(2-methyl-allyloxy)-phenyl]-1H-benzimidazole:

To a mixture of 2(1H-benzimidazol-2-yl)-4-methoxy-phenol) (3.6 g, 0.015 mole) and potassium carbonate (2.35 g, 0.017 mole) in 20 ml of DMF heated to 85° C., is added methallyl chloride (1.36 g, 0.015 mole) drop by drop over a 20-minute period. It is left at 85° C. for 4 hours. The reaction mixture is cooled and poured into ice cold water. The resulting precipitate is filtered, washed in water, and recrystallized in methanol. We obtain 2.3 g (yield=52%) of a pale yellow powder of 2-[5-methoxy-2-(2-methyl-allyloxy)-phenyl]-1H-benzimidazole:

Mp: 144–148° C.

b) Second stage: preparation of 2-(1H-benzimidazol-2-yl) -4-methoxy-6-(2-methyl-allyl)-phenol:

The foregoing derivative (2 g) is heated to 180° C. for 2 hours and 30 minutes. After cooling, the reaction mixture is silica-chromatographed (eluent: dichloromethane). We thus obtain 2 g of a pale yellow powder of 2-(1H-benzimidazol-2-yl)-4-methoxy-6-(2-methyl-allyl)-phenol:

| | |
|---|---|
| Mp: 127–129° C. | |
| UV (ethanol) | $\lambda_{max}$ = 302 nm, $\epsilon_{max}$ = 18,500 |
| | $\lambda_{max}$ = 343 nm, $\epsilon_{max}$ = 16,200 |

Ultimate analysis for $C_{18}H_{18}N_2O_2$

| | | | | |
|---|---|---|---|---|
| theoretical | C 73.45 | H 6.16 | N 9.52 | O 10.87 |
| actual | C 73.34 | H 6.16 | N 9.52 | O 11.02 |

c) Third stage: preparation of the derivative of example 1

To a solution of the foregoing derivative (1.47 g, 0.005 mole) and catalyst (complex with 3–3.5% by weight of Pt in cyclovinylmethylsiloxane by Hüls Petrarch, PC085: 120 μl) in 3 ml of dry toluene heated to 80° C. is added 1.22 g (0.0055 mole) of heptamethyltrisiloxane drop by drop over a 20-minute period. It is left at this temperature for 5 hours. The reaction mixture is concentrated and one obtains after silica chromatography (eluent: Heptane/$CH_2Cl_2$ 30:70) 0.5 g of a colorless oil of the derivative of example 1:

| | |
|---|---|
| UV (ethanol) | $\lambda_{max}$ = 302 nm, $\epsilon_{max}$ = 17,780<br>$\lambda_{max}$ = 343 nm, $\epsilon_{max}$ = 15,060 |

Ultimate analysis for $C_{25}H_{40}N_2O_4Si_3$

| | | | | |
|---|---|---|---|---|
| theoretical | C 59.83 | H 7.83 | N 2.79 | Si 16.79 |
| actual | C 60.02 | H 7.71 | N 2.72 | Si 16.57 |

EXAMPLE 2

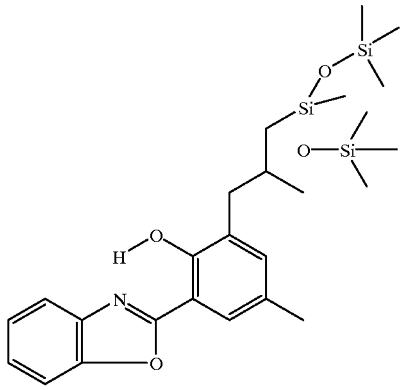

a) First stage: preparation of 2-[5-methyl-2-(2-methyl-allyloxy)-phenyl]-benzoxazole To a mixture of 2-benzoxazol-2-yl-4-methyl-phenol (5.63 g, 0.025 mole) and potassium carbonate (3.8 g, 0.0275 mole) in 50 ml of DMF heated to 80° C. is added methallyl chloride (2.49 g, 0.0275 mole) drop by drop over a 20-minute period. It is left at 80° C. for 2 hours. The reaction mixture is cooled and poured into glacial water. Extraction is performed with dichloromethane, the organic phase is dried, and the solvent evaporated. The resulting powder of 2-[5-methyl-2-(2-methyl-allyloxy)-phenyl]-benzoxazole (Mp: 57–58° C.) is treated directly in the next stage.

b) Second stage: preparation of 2-benzoxazol-2-yl-4-methyl-6-(2-methyl-allyl)-phenol The foregoing derivative is heated to 190° C. for 6 hours. After cooling, the reaction mixture is silica-chromatographed (eluent: dichloromethane). We thus obtain 4.5 g of a pale yellow powder of 2-benzoxazol-2-yl-4-methyl-6-(2-methyl-allyl)-phenol:

| | |
|---|---|
| Mp: 81–83° C. | |
| UV (ethanol) | $\lambda_{max}$ = 299 nm, $\epsilon_{max}$ = 20,130<br>$\lambda_{max}$ = 333 nm, $\epsilon_{max}$ = 14,180 |

Ultimate analysis for $C_{18}H_{17}NO_2$

| | | | | |
|---|---|---|---|---|
| theoretical | C 77.40 | H 6.13 | N 5.01 | O 11.46 |
| found | C 77.36 | H 6.06 | N 4.90 | O 11.60 |

c) Third stage: preparation of the derivative of example 2

To a solution of the foregoing derivative (3.8 g, 0.0136 mole) and catalyst (complex with 3–3.5% by weight of Pt in cyclovinylmethylsiloxane by Hüls Petrarch, PC085: 20 μl) in 10 ml of dry toluene heated to 80° C. is added 3.1 g (0.014 mole) of heptamethyltrisiloxane drop by drop over a 20-minute period. It is left at this temperature for 8 hours. The reaction mixture is concentrated and one obtains after column chromatography purification (eluent: Heptane/Dichloromethane 40/60) 3.7 g (yield: 56%) of a white powder of the derivative of example 2:

| | |
|---|---|
| Mp: 53–54° C. | |
| UV (ethanol) | $\lambda_{max}$ = 287 nm, $\epsilon_{max}$ = 19,980<br>$\lambda_{max}$ = 300 nm, $\epsilon_{max}$ = 24,150<br>$\lambda_{max}$ = 333 nm, $\epsilon_{max}$ = 13,830 |

Ultimate analysis for $C_{24}H_{37}NO_4Si_3$

| | | | | |
|---|---|---|---|---|
| theoretical | C 59.09 | H 7.65 | N 2.87 | Si 17.27 |
| found | C 58.99 | H 7.85 | N 2.80 | Si 17.20 |

EXAMPLE 3

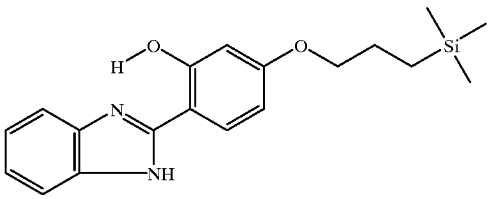

a) First stage: preparation of methyl 2-hydroxy-4-(3-trimethylsilanyl-propyloxy)-benzoate To a mixture of methyl gentisate (16.8 g, 0.1 mole) and potassium carbonate (15.2 g, 0.11 mole) in 80 ml of DMF in a nitrogen atmosphere at 80° C. is added chloropropyl trimethyl silane (16.6 g, 0.11 mole) drop by drop over a 20-minute period. The mixture is heated to 90° C. for 8 hours. It is cooled and then poured into 200 ml of water. Extraction is performed with diisopropyl ether. The organic phase is washed with water, dried with sodium sulfate, and then concentrated. After silica chromatography of the resulting yellow oil (eluent: Heptane/$CH_2Cl_2$ 90:10) we obtain 3.3 g of a clean fraction of methyl 2-hydroxy-4-(3-trimethylsilanyl-propyloxy)-benzoate.

Ultimate analysis for $C_{14}H_{22}O_4Si$

| | | | |
|---|---|---|---|
| calculated | C 59.54 | H 7.85 | Si 9.94 |
| found | C 59.31 | H 7.93 | Si 10.20 |

b) Second stage: preparation of the derivative of example 3

A mixture of the foregoing derivative (2 g, 0.0071 mole), ortho phenylene diamine (10 g), and boric acid (0.05 g) in 3 ml of N-methyl pyrrolidone is raised to 170° C. with bubbling nitrogen for 3 hours. The reaction mixture is cooled and poured into water. The purple precipitate of excess ortho phenylene diamine is filtered out. The liquor is concentrated and chromatographed (eluent: dichloromethane) to yield the derivative of example 3:

| | |
|---|---|
| Mp: 202–208° C. | |
| UV (ethanol) | $\lambda_{max}$ = 333 nm, $\epsilon_{max}$ = 22,200 |
| | $\lambda_{max}$ = 318 nm, $\epsilon_{max}$ = 24,250 |

Ultimate analysis for $C_{19}H_{24}N_2O_2Si$

| | | | | |
|---|---|---|---|---|
| calculated | C 67.02 | H 7.10 | N 8.23 | Si 8.25 |
| found | C 67.35 | H 7.02 | N 8.11 | Si 8.02 |

EXAMPLE 4

Here we give a concrete example of a cosmetic composition according to the invention, that is, a sunscreen O/W emulsion:

| | |
|---|---|
| compound of example 1 | 4% |
| mixture of ceylstearyl alcohol and cetylstearyl oxyethylenated alcohol (33 OE) 80/20 sold under the tradename of "Dehsconet 390" by Tensia | 7% |
| mixture of glycerol mono and distearate sold under the tradename of "Cerasynth SD" by ISP | 2% |
| cetyl alcohol | 1.5% |
| polydimethylsiloxane sold under the tradename of "DC200 Fluid" by Dow Corning | 1.5% |
| alcohol benzoate at $C_{12}$–$C_{15}$ sold under the tradename of "Finsolv TN" by Finetex | 16% |
| glycerine | 20% |
| preservatives | in sufficient quantity |
| deionized water | sufficient quantity for 100% |

This O/W emulsion is prepared according to the conventional emulsion preparation techniques by dissolving the filter in the fatty phase containing the emulsifiers, by heating the fatty phase to 70–80° C., and by adding water heated to the same temperature with vigorous agitation. The agitation is maintained for 10 to 15 minutes, then it is allowed to cool with moderate agitation, and then finally, at 40° C., the preservatives are added.

In this way a sunscreen creme particularly effective against UV B and UV A is obtained.

What is claimed is:

1. A liposoluble, photostable, UV-photoprotecting benz-x-azole-substituted silane or siloxane having the formula (1) or (2):

(1)

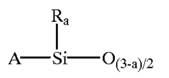 or $A—SiR'_1R'_2R'_3$ (2)

in which R is a $C_1$–$C_{30}$ saturated or unsaturated hydrocarbyl radical, a $C_1$–$C_8$ halogenated hydrocarbyl radical, or a trimethylsilyloxy radical; a is 1 or 2; the radicals $R'_1$, $R'_2$ and $R'_3$ are independently a $C_1$–$C_8$ linear or branched alkyl or alkenyl radical; and A is a radical having the structural formula (I):

(I)

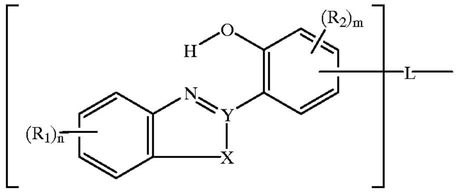

in which L is a divalent radical bonding said radical A to the silicon atom in the structural formula (1); the radicals $R_1$ and $R_2$ are independently a hydrogen atom, a $C_1$–$C_{10}$ linear or branched alkyl radical or a $C_2$–$C_8$ linear or branched alkenyl radical, wherein two adjacent $R_1$ or $R_2$ radicals are as defined above or together form an alkylidenedioxy radical wherein the alkylidene moiety has 1 or 2 carbon atoms; Y is C or N; and X is O, $NR_3$, S when Y is C, or C when Y is N, wherein $R_3$ is a hydrogen atom, or a $C_1$–$C_8$ alkyl radical; and n and m are, independently, 0 or 1.

2. The benz-x-azole-substituted silane or siloxane as defined by claim 1, wherein formula (I), L is one of the following divalent radicals (a) or (a'):

(a)

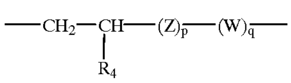

(a')

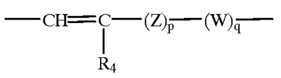

in which W is O or NH; Z is a $C_1$–$C_6$ linear or branched, saturated or unsaturated divalent hydrocarbyl radical, or a substituted such radical bearing a hydroxyl substituent, or a $C_2$–$C_8$ linear or branched, saturated or unsaturated hydrocarbyl radical; $R_4$ is a hydrogen atom, a hydroxyl radical, or a $C_1$–$C_8$ linear or branched, saturated or unsaturated hydrocarbyl radical; and p and q are each 0 or 1.

3. The benz-x-azole-substituted siloxane as defined by claim 2, having one of the formulae (3) or (4):

(3)

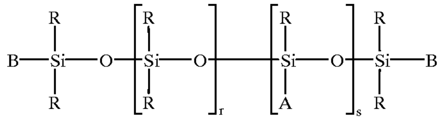

(4)

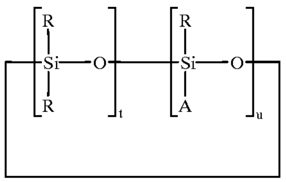

in which R is a $C_1$–$C_{30}$ saturated or unsaturated hydrocarbyl radical, a $C_1$–$C_8$ halogenated hydrocarbyl radical, or a trimethylsilyloxy radical; the radicals B, which may be identical or different, are each a radical R or a radical A; r is a whole number ranging from 0 to 50, inclusive; s is a whole number ranging from 0 to 20, inclusive, with the proviso that, if s is 0, then at least one of the radicals B is a radical A; u is a whole number ranging from 1 to 6, inclusive; t is a whole number ranging from 0 to 10, inclusive; and t+u is equal to or greater than 3.

4. The benz-x-azole-substituted siloxane as defined by claim 3, wherein formulae (3) or (4), the radicals R are independently a $C_1$–$C_{10}$ linear or branched, saturated or unsaturated hydrocarbyl radical, a phenyl radical, or a 3,3,3-trifluoropropyl radical, with the proviso that at least 80% of the radials R are methyl radicals.

5. The benz-x-azole-substituted siloxane as defined by claim 3, wherein formulae (3) or (4), at least one of the following conditions is satisfied:

R is methyl,

B is methyl, $R_1$ is H, $R_2$ is methyl or methoxy, p is 1, q is 0 or 1,

W is 0, r ranges from 0 to 3, inclusive, s ranges from 1 to 3 inclusive, t+u ranges from 3 to 5, and/or $R'_1$, $R'_2$, and $R'_3$ are methyl.

6. The benz-x-azole-substituted siloxane as defined by claim 3, having the formula (3).

7. The benz-x-azole-substituted siloxane as defined by claim 3, having the formula (4).

8. The benz-x-azole-substituted siloxane as defined by claim 1, having the formula (1).

9. The benz-x-azole-substituted silane as defined by claim 1, having the formula (2).

10. The benz-x-azole-substituted silane or siloxane as defined by claim 2, wherein formula (I), L is a divalent radical (a).

11. The benz-x-azole-substituted silane or siloxane as defined by claim 2, wherein formula (I), L is a divalent radical (a').

12. The benz-x-azole-substituted silane or siloxane as defined by claim 1, wherein formula (I), Y is C.

13. The benz-x-azole-substituted silane or siloxane as defined by claim 1, wherein formula (I), Y is N.

14. The benz-x-azole-substituted silane or siloxane as defined by claim 1, wherein formula (I), X is O.

15. The benz-x-azole-substituted silane or siloxane as defined by claim 1, wherein formula (I), X is $NR_3$.

16. The benz-x-azole-substituted silane or siloxane as defined by claim 1, wherein formula (I), X is S and Y is C.

17. The benz-x-azole-substituted silane or siloxane as defined by claim 1, wherein formula (I), X is C and Y is N.

18. A process for the preparation of a benz-x-azole-substituted silane or siloxane as defined by claim 2, comprising hydrosilylating, in the presence of a catalytically effective amount of a platinum hydrosilylation catalyst, a silane or siloxane compound having the formula (1') or (2'):

(1')

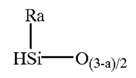

with a benz-x-azole compound having the structural formula (I'):

(I')

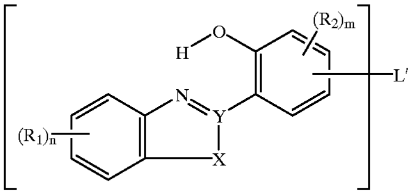

wherein L' is one of the following radicals (b) or (b'):

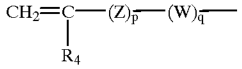

(b)

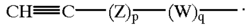

(b')

$CH\equiv C—(Z)_p—(W)_q—$ (b').

19. A process for the preparation of a benz-x-azole-substituted siloxane as defined by claim 3, having one of the formulae (3) or (4), comprising hydrosilylating, in the presence of a catalytically effective amount of a platinum hydrosilylation catalyst, a siloxane compound having the formula (6) or (7):

(6)

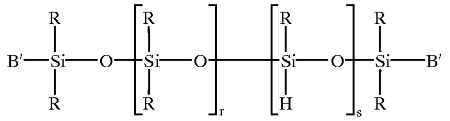

or (7)

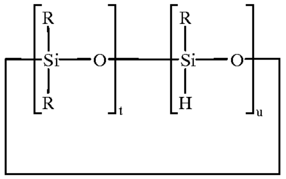

wherein the radicals B' are independently a radical R or a hydrogen atom, with a benz-x-azole compound having the structural formula (I'):

(I')

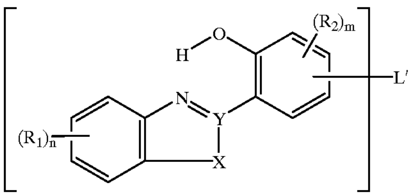

wherein L' is one of the following radicals (b) or (b'):

(b)

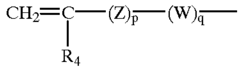

or

-continued $CH{\equiv}C—(Z)_p—(W)_q—\cdot$ (b')

$CH{\equiv}C—(Z)_p—(W)_q—$ (b').

20. A process for the preparation of a silane having the following formula (2):

$A—SiR'_1R'_2R'_3$ (2)

in which the radicals $R'_1$, $R'_2$ and $R'_3$ are independently a $C_1$–$C_8$ linear or branched alkyl or alkenyl radical; and A is a radical having the structural formula (I):

(I)

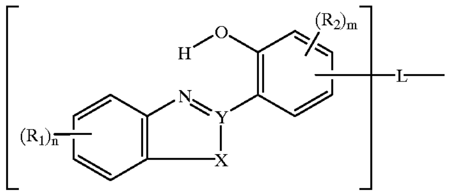

in which L is a divalent radical bonding said radical A to the silicon atom; the radicals $R_1$ and $R_2$ are independently a hydrogen atom, a $C_1$–$C_{10}$ linear or branched alkyl radical or a $C_2$–$C_8$ linear or branched alkenyl radical, wherein two adjacent $R_1$ or $R_2$ radicals are as defined above or together form an alkylidenedioxy radical wherein the alkylidene moiety has 1 or 2 carbon atoms; Y is C or N; and X is O, $NR_3$, S when Y is C, or C when Y is N, wherein $R_3$ is a hydrogen atom, or a $C_1$–$C_8$ alkyl radical; and n and m are, independently, 0 or 1, comprising reacting a benz-x-azole compound having the structural formula (c):

(c)

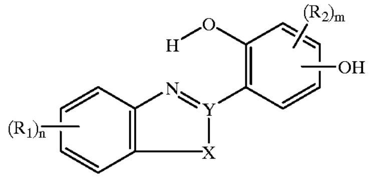

with a silane compound having the formula (8):

$Hal—(Z)_p—CHR_4—CH_2—SiR'_1R'_2R'_3$ (8)

in which Hal is a halogen atom; Z is a $C_1$–$C_6$ linear or branched, saturated or unsaturated divalent hydrocarbyl radical, or a substituted such radical bearing a hydroxyl substituent, or a $C_2$–$C_8$ linear or branched, saturated or unsaturated hydrocarbyl radical; $R_4$ is a hydrogen atom, a hydroxyl radical, or a $C_1$–$C_8$ linear or branched, saturated or unsaturated hydrocarbyl radical; and p is 0 or 1.

21. A process for the preparation of a silane having the following formula (2):

$A—SiR'_1R'_2R'_3$ (2)

in which the radicals $R'_1$, $R'_2$ and $R'_3$ are independently a $C_1$–$C_8$ linear or branched alkyl or alkenyl radical; and A is a radical having the structural formula (I):

(I)

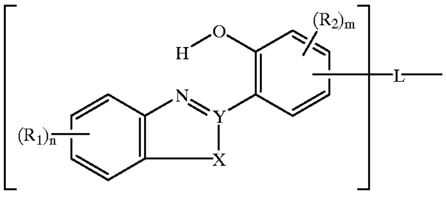

in which L is a divalent radical bonding said radical A to the silicon atom; the radicals $R_1$ and $R_2$ are independently a hydrogen atom, a $C_1$–$C_{10}$ linear or branched alkyl radical or a $C_2$–$C_8$ linear or branched alkenyl radical, wherein two adjacent $R_1$ or $R_2$ radicals are as defined above or together form an alkylidenedioxy radical wherein the alkylidene moiety has 1 or 2 carbon atoms; Y is C or N; and X is O, $NR_3$, S when Y is C, or C when Y is N, wherein $R_3$ is a hydrogen atom, or a $C_1$–$C_8$ alkyl radical; and n and m are, independently, 0 or 1, comprising condensing a compound having the formula (9):

(9)

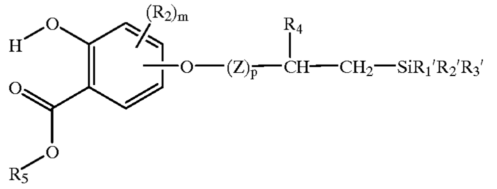

in which Z is a $C_1$–$C_6$ linear or branched, saturated or unsaturated divalent hydrocarbyl radical, or a substituted such radical bearing a hydroxyl substituent, or a $C_2$–$C_8$ linear or branched, saturated or unsaturated hydrocarbyl radical; $R_4$ is a hydrogen atom, a hydroxyl radical, or a $C_1$–$C_8$ linear or branched, saturated or unsaturated hydrocarbyl radical; $R_5$ is a hydrogen atom or methyl radical; and p is 0 or 1, with a compound having the formula (10):

(10)

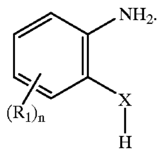

22. A photostable sunscreen or cosmetic composition suited for the UV-photoprotection of human skin, hair or both, comprising an effective UV-photoprotecting amount of at least one benz-x-azole-substituted silane or siloxane having the formula (1) or (2):

(1)

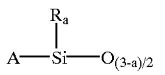 or $A—SiR'_1R'_2R'_3$ (2)

in which R is a $C_1$–$C_{30}$ saturated or unsaturated hydrocarbyl radical, a $C_1$–$C_8$ halogenated hydrocarbyl radical, or a trimethylsilyloxy radical; a is 1 or 2; the radicals $R'_1$, $R'_2$ and $R'_3$, which may be identical or different, are each a $C_1$–$C_8$ linear or branched alkyl or alkenyl radical; and A is a radical having the structural formula (I):

(I)

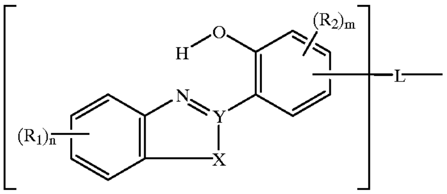

in which L is a divalent radical bonding said radical A to the silicon atom; the radicals $R_1$ and $R_2$, which may be identical or different, are each a hydrogen atom, a $C_1$–$C_{10}$ linear or branched alkyl radical, a $C_2$–$C_8$ linear or branched alkenyl radical, with the proviso that two adjacent $R_1$ or $R_2$ radicals may together form an alkylidenedioxy radical wherein the alkylidene moiety has 1 or 2 carbon atoms; Y is C or N; and X is O, $NR_3$, S when Y is C, or C when Y is N, wherein $R_3$ is a hydrogen atom, or a $C_1$–$C_8$ alkyl radical; and n and m are, independently, 0 or 1, formulated into a topically applicable, cosmetically acceptable medium therefor.

23. The sunscreen or cosmetic composition as defined by claim 22, comprising from 0.1% to 20% by weight of said at least one benz-x-azole-substituted silane or siloxane (1) or (2).

24. The sunscreen or cosmetic composition as defined by claim 23, comprising from 0.5% to 10% by weight of said at least one benz-x-azole-substituted silane or siloxane (1) or (2).

25. The sunscreen or cosmetic composition as defined by claim 22, comprising an oil-in-water emulsion.

26. The sunscreen or cosmetic composition as defined by claim 22, comprising a water-in-oil emulsion.

27. The sunscreen or cosmetic composition as defined by claim 22, further comprising at least one additional hydrophilic or lipophilic organic UV-A and/or UV-B sunscreen.

28. The sunscreen or cosmetic composition as defined by claim 27, further comprising at least one cinnamic sunscreen, salicylic sunscreen, camphor sunscreen, triazine sunscreen, benzophenone sunscreen, dibenzoylmethane sunscreen, β,β-diphenyl-acrylate sunscreen, p-aminobenzoic acid sunscreen, sunscreen polymer or sunscreen silicone.

29. The sunscreen or cosmetic composition as defined by claim 22, further comprising a UV-photoprotecting effective amount of particulates of at least one inorganic pigment or nanopigment.

30. The sunscreen or cosmetic composition as defined by claim 29, said at least one pigment or nanopigment comprising titanium dioxide, zinc oxide, iron oxide, zirconium oxide, cerium oxide, or mixture thereof.

31. The sunscreen or cosmetic composition as defined by claim 22, further comprising at least one active agent for the artificial tanning or darkening of human skin, or for the artificial tanning and darkening of human skin.

32. The sunscreen or cosmetic composition as defined by claim 22, further comprising at least one cosmetically acceptable adjuvant or additive.

33. The sunscreen or cosmetic composition as defined by claim 32, said at least one adjuvant or additive comprising a fat, organic solvent, thickening agent, softener, silicone, anti-foaming agent, hydrating agent, fragrance, preservative, surfactant, filler, complexing agent, polymer, propellant, basifying or acidifying agent, dye, pigment, or mixture thereof.

34. The sunscreen or cosmetic composition as defined by claim 22, comprising a vesicular dispersion, lotion, cream, milk, gel, ointment, suspension, paste, dispersion, powder, solid stick, foam or spray.

35. The sunscreen or cosmetic composition as defined by claim 22, comprising a makeup.

36. The sunscreen or cosmetic composition as defined by claim 35, comprising an anhydrous or aqueous solid or paste, emulsion, suspension or dispersion.

37. The sunscreen or cosmetic composition as defined by claim 22, comprising a shampoo, lotion, gel, emulsion, vesicular dispersion, hair dye or bleach, hair spray, or rinse.

38. A method for protecting human skin, hair or both against the deleterious effects of ultraviolet irradiation, comprising topically applying thereto an effective UV-photoprotecting amount of the sunscreen/cosmetic composition as defined by claim 22.

39. A method for protecting human skin, hair or both against the deleterious effects of solar radiation, comprising topically applying thereto an effective UV-photoprotecting amount of the sunscreen/cosmetic composition as defined by claim 22.

40. A liposoluble, photostable, UV-photoprotecting benz-x-azole-substituted silane or siloxane having the formula (1) or (2):

(1)

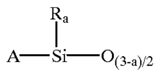

or $A—SiR'_1R'_2R'_3$ (2)

in which R is a $C_1$–$C_{30}$ saturated or unsaturated hydrocarbyl radical, a $C_1$–$C_8$ halogenated hydrocarbyl radical, or a trimethylsilyloxy radical; a is 1 or 2; the radicals $R'_1$, $R'_2$ and R'3 are independently a $C_1$–$C_8$ linear or branched alkyl or alkenyl radical; and A is a radical having the structural formula (I):

(I)

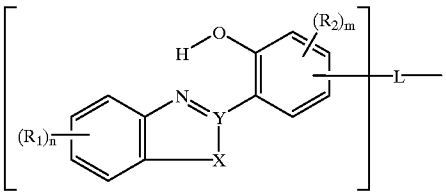

in which L is a divalent radical (a) or (a');

(a)

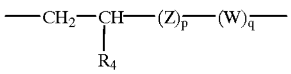

or (a')

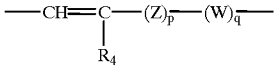

in which W is O or NH; Z is a $C_1$–$C_6$ linear or branched, saturated or unsaturated divalent hydrocarbyl radical, or a substituted such radical bearing a hydroxyl substituent, or a $C_2$–$C_8$ linear or branched, saturated or unsaturated hydrocarbyl radical; $R_4$ is a hydrogen atom, a hydroxyl radical, or a $C_1$–$C_8$ linear or branched, saturated or unsaturated hydrocarbyl radical; and p and q are each 0 or 1; the radicals $R_1$ and $R_2$ are independently a hydrogen atom, a $C_1$–$C_{10}$ linear or branched alkyl radical or a $C_2$–$C_8$ linear or branched alkenyl radical, wherein two adjacent $R_1$ or $R_2$ radicals are as defined above or together form an alkylidenedioxy radical wherein the alkylidene moiety has 1 or 2 carbon atoms; Y is C or N; and X is O, $NR_3$, S when Y is C, or C when Y is N, wherein $R_3$ is a hydrogen atom, or a $C_1$–$C_8$ alkyl radical; and n and m are, independently, 0 or 1.

41. The process according to claim 21, where the compound having the formula (9) is reacted with the compound having the formula (10) in the presence of boric acid.

* * * * *